United States Patent
Kim et al.

(10) Patent No.: US 10,309,937 B2
(45) Date of Patent: Jun. 4, 2019

(54) METHOD FOR DETECTING IMPURITIES IN AMMONIUM HYDROXIDE

(71) Applicant: Samsung Electronics Co., Ltd., Suwon-si, Gyeonggi-do (KR)

(72) Inventors: Kihyun Kim, Suwon-si (KR); Sooyeon Kim, Hwaseong-si (KR); JungDae Park, Yongin-si (KR); Min Soo Suh, Hwaseong-si (KR); Hyang Bong Lee, Hwaseong-si (KR); Kwangshin Lim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 104 days.

(21) Appl. No.: 15/393,731

(22) Filed: Dec. 29, 2016

(65) Prior Publication Data
US 2017/0219538 A1    Aug. 3, 2017

(30) Foreign Application Priority Data

Feb. 3, 2016  (KR) .................. 10-2016-0013616

(51) Int. Cl.
  *G01N 30/06* (2006.01)
  *G01N 30/16* (2006.01)
  (Continued)

(52) U.S. Cl.
  CPC .............. *G01N 30/06* (2013.01); *C01C 1/28* (2013.01); *G01N 2030/067* (2013.01); *G01N 2030/8872* (2013.01)

(58) Field of Classification Search
  CPC .. G01N 30/06; G01N 30/16; G01N 2030/027; G01N 2030/067; G01N 2030/8872; C01C 1/28
  See application file for complete search history.

(56) References Cited

U.S. PATENT DOCUMENTS

| 5,167,827 A | 12/1992 | Glatz |
| 6,534,027 B2 | 3/2003 | Dershowitz et al. |

(Continued)

FOREIGN PATENT DOCUMENTS

| JP | 2808982 | 12/1993 |
| JP | 2000-218148 | 8/2000 |

(Continued)

OTHER PUBLICATIONS

Waterman, Kenneth C. et al. "Stabilization of pharmaceuticals to oxidative degradation." Pharmaceutical Development and Technology (2002). (Year: 2002).*

(Continued)

*Primary Examiner* — Christopher Adam Hixson
(74) *Attorney, Agent, or Firm* — Sughrue Mion, PLLC

(57) ABSTRACT

Provided is a method for detecting impurities in ammonium hydroxide. The method for detecting impurities in ammonium hydroxide includes preparing a potassium permanganate solution, preparing ammonium hydroxide, and adding the potassium permanganate solution several times to the ammonium hydroxide so as to detect impurities in the ammonium hydroxide. Potassium permanganate contained in the potassium permanganate solution is added for each time in the range of 0.0001 mol to 0.01 mol per 1 g of ammonia contained in the ammonium hydroxide.

14 Claims, 6 Drawing Sheets

(51) Int. Cl.
    *C01C 1/28*     (2006.01)
    *G01N 30/88*    (2006.01)

(56)           References Cited

U.S. PATENT DOCUMENTS

| 6,939,527 | B2 | 9/2005 | Oeter et al. |
| 2005/0250172 | A1 | 11/2005 | Nozaki et al. |
| 2008/0300233 | A1* | 12/2008 | Kroselj ............... A61K 9/2018 514/210.02 |
| 2012/0161974 | A1 | 6/2012 | Trost et al. |
| 2015/0021491 | A1 | 1/2015 | Higashi et al. |

FOREIGN PATENT DOCUMENTS

| JP | 3824904 | 4/2003 |
| JP | 2004-125453 | 4/2004 |
| JP | 3745743 | 11/2004 |
| JP | 4498186 | 10/2006 |
| KR | 10-2000-0059510 | 10/2000 |
| KR | 10-0506812 | 10/2006 |

OTHER PUBLICATIONS

Wyndham, Kevin D. et al. "Characterization and evaluation of C18 HPLC stationary phases based on ethyl-bridged hybrid organic/inorganic particles." Analytical Chemistry (2003) 75 6781-6788. (Year: 2003).*

The Chromatography Forum website, posted in 2001, obtained by the examiner at <http://http://www.lcresources.com/discus/messages/5133/1876.html?SaturdayAugust420011108am> on Sep. 29, 2018. (Year: 2001).*

* cited by examiner

METHOD FOR DETECTING IMPURITIES IN AMMONIUM HYDROXIDE

CROSS-REFERENCE TO RELATED APPLICATIONS

This U.S. nonprovisional patent application claims priority under 35 U.S.C. § 119 to Korean Patent Application 10-2016-0013616 filed on Feb. 3, 2016, the entire contents of which are hereby incorporated by reference.

BACKGROUND

The present inventive concept relates to a method for detecting impurities in ammonium hydroxide.

Various kinds of chemicals are used in manufacturing processes for highly integrated semiconductor devices. For example, ammonium hydroxide (NH$_4$OH) is utilized to remove polysilicon in the manufacturing process for semiconductor devices. The semiconductor devices may suffer from impurities contained in the ammonium hydroxide. For example, in the manufacturing process for semiconductor devices, a silicon gate may be formed to serve as a dummy gate. The ammonium hydroxide may remove the silicon gate to form a metal gate. However, impurities contained in the ammonium hydroxide may cause damage to not only the polysilicon but also to the metal and its nitride, such as TiN, thus reducing the reliability of the semiconductor device.

SUMMARY

Embodiments of the present inventive concept provide a method for detecting impurities having a low concentration in ammonium hydroxide.

According to exemplary embodiments of the present inventive concept, a method for detecting impurities in ammonium hydroxide may include: preparing a potassium permanganate solution; preparing ammonium hydroxide; and adding the potassium permanganate solution several times to the ammonium hydroxide in order to detect impurities in the ammonium hydroxide. Potassium permanganate contained in the potassium permanganate solution may be added for each time in the range of 0.0001 mol to 0.01 mol per 1 g of ammonia contained in the ammonium hydroxide.

According to other exemplary embodiments of the present inventive concept, a method for detecting impurities in ammonium hydroxide may include: preparing ammonium hydroxide having a concentration in the range of 1 wt % to 5 wt %; preparing a liquid chromatography separation system including a stationary phase and water; and injecting the ammonium hydroxide into the liquid chromatography separation system. The stationary phase may include: silica; and a functional group that is combined with a surface of the silica and is represented by the following chemical formula

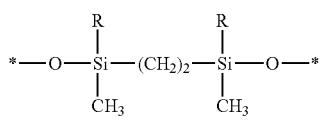

In some embodiments, R may be n-octadecyl, and a symbol of * may mean that the functional group is combined with the surface of silica.

According to yet other exemplary embodiments of the present inventive concept, a method for detecting impurities in ammonium hydroxide may include: injecting ammonium hydroxide having a concentration in the range of 1 wt % to 5 wt % into a liquid chromatography separation system, wherein the liquid chromatography separation system includes a stationary phase and water; and wherein the stationary phase includes silica and a functional group combined with a surface of the silica having the following chemical formula:

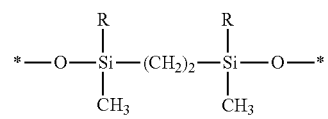

wherein, R is n-octadecyl, and a symbol of * means that the functional group is combined with the surface of silica.

BRIEF DESCRIPTION OF THE DRAWINGS

The accompanying drawings are included to provide a further understanding of the invention, and are incorporated in and constitute a part of this specification. The drawings illustrate example embodiments of the present invention and, together with the description, serve to explain principles of the present invention. In the drawings.

DETAILED DESCRIPTION OF EMBODIMENTS

Hereinafter, it will be described about a method for detecting impurities in ammonium hydroxide according to exemplary embodiments of the present inventive concept.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, but do not preclude the presence or addition of one or more other features unless otherwise indicated herein.

The term "about" can allow for a degree of variability in a value or range, for example, within 20%, within 15%, within 10%, within 5%, 4%, 3%, 2% or within 1% of a stated value or of a stated limit of a range. When a range or a list of sequential values is given, unless otherwise specified any value within the range or any value between the given sequential values is also disclosed.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Figure 1:
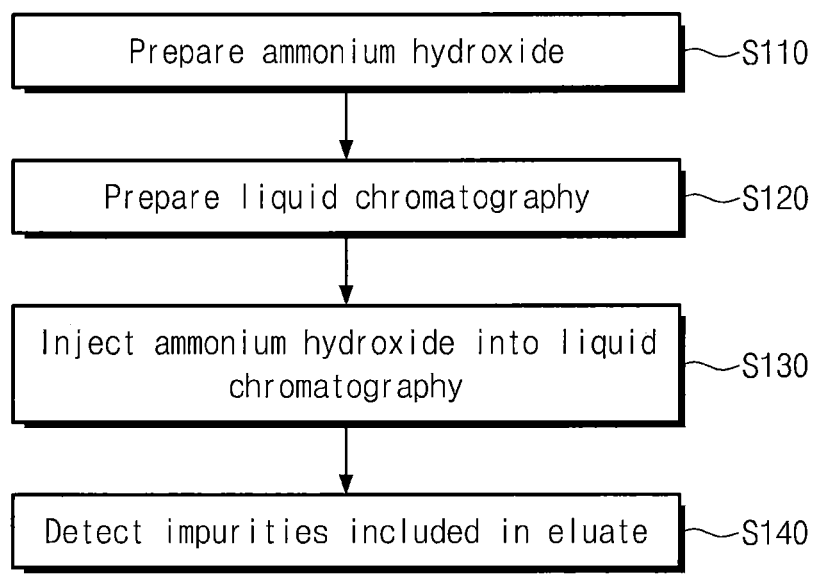
FIG. 1 is a flow chart illustrating a method for detecting impurities in ammonium hydroxide according to exemplary embodiments of the present inventive concept.

FIG. 1 is a flow chart illustrating a method for detecting impurities in ammonium hydroxide according to exemplary embodiments of the present inventive concept. A repetitive description will be hereinafter omitted.

Referring to FIG. 1, ammonium hydroxide may be prepared (S110). Impurities may also be formed in the preparation of ammonium hydroxide. The impurities contained in ammonium hydroxide may include an oxidizer such as hydrogen peroxide ($H_2O_2$), ions, particles, or the like, but the present embodiment is not limited thereto. For example, the impurities may include various materials that can interact with a stationary phase of a liquid chromatography separation system which will be discussed below. The concentration of ammonium hydroxide may be adjusted. For example, ammonium hydroxide may have a concentration in the range of about 1 wt % or about 5 wt %.

A liquid chromatography separation system may be prepared (S120). The liquid chromatography separation system may be prepared by adding a stationary phase to a solvent. The solvent may include water of 100 wt % and may serve as a mobile phase. The term of water may mean deionized water (DIW). The stationary phase may include a silica support and a functional group represented by the following chemical formula 1 that is combined with a surface of the silica support.

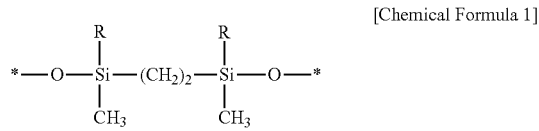

[Chemical Formula 1]

wherein, R is n-octadecyl and a symbol of * means that the functional group is combined with the surface of silica support.

The silica support may be, but not limited to silica gel or bonded silica gel. The stationary phase may be in the form of particles and may have any suitable particle size. For example, the average particle size of the stationary phase can equal to or less than about 1 μm, 5 μm, 10 μm, 50 μm, 100 μm, 150 μm, 200 μm, 250 μm, 300 μm, 350 μm, 400 μm, 450 μm, 500 μm, 600 μm, 700 μm, 800 μm, 900 μm, 1 mm, 2 mm, 3 mm, 4 mm, 5 mm, 10 mm, about 50 mm, or more. The stationary phase can have any suitable surface area. For example, the average surface area of the stationary phase can be equal to or less than about 1 m$^2$/g, 10 m$^2$/g, 20 m$^2$/g, 50 m$^2$/g, 100 m$^2$/g, 150 m$^2$/g, 200 m$^2$/g, 250 m$^2$/g, 300 m$^2$/g, 350 m$^2$/g, 400 m$^2$/g, 450 m$^2$/g, 500 m$^2$/g, 550 m$^2$/g, 600 m$^2$/g, 700 m$^2$/g, 800 m$^2$/g, 900 m$^2$/g, 1000 m$^2$/g, or more. The stationary phase can have any suitable average pore size, and any suitable range of pore sizes. For example, the stationary phase can have a pore size of equal to or less than about 1 Å, 2 Å, 5 Å, 10 Å, 20 Å, 30 Å, 40 Å, 50 Å, 60 Å, 70 Å, 80 Å, 90 Å, 100 Å, 150 Å, 200 Å, 250 Å, 300 Å, 500 Å, 750 Å, 1000 Å, 1 μm, 10 μm, 25 μm, 50 μm, 75 μm, or about 100 μm or more, or any combination thereof. The stationary phase can have any suitable range of pore volume, and any suitable range of pore volumes. For example, the stationary phase can have a pore volume equal to or less than about 0.01 cm$^3$/g, 0.1 cm$^3$/g, 0.2 cm$^3$/g, 0.3 cm$^3$/g, 0.4 cm$^3$/g, 0.5 cm$^3$/g, 0.6 cm$^3$/g, 0.7 cm$^3$/g, 0.8 cm$^3$/g, 0.9 cm$^3$/g, 1.0 cm$^3$/g, 1.5 cm$^3$/g, 2.0 cm$^3$/g, 5.0 cm$^3$/g, 10.0 cm$^3$/g.

The liquid chromatography separation system may be in the form of a column. As one of ordinary skill in the art will readily appreciate, liquid chromatography is generally performed in a cylindrical encasement having the shape of a column. The encasement can be any suitable material, such as, for example, glass, metal, plastic, and the like. Any suitable column shape can be used. A taller column can be used, for example, to increase the residence time of the mixture in the stationary phase as the mobile phase is eluted at a given rate. A wider column can be used, for example, to allow for the use of a greater quantity of stationary phase for a given column height. In some examples, increasing the quantity of stationary phase for a given column height or increasing the residence time at a given elution rate can allow for the separation of a larger amount of the mixture to be separated or it can allow for the desired degree of separation that have smaller differences in relative attraction to the mobile phase versus the stationary phase. The height of the column can be any suitable height, such as less than or equal to 100 mm, 250 mm, 500 mm, 750 mm, 1 m, 2 m, 3 m, 4 m, 5 m, 6 m, 7 m, 8 m, 9 m, 10 m, 11 m, 12 m, 13 m, 14 m, or about 15 m, or more. In some embodiments, a column can have any suitable height, including by using several discrete columns linked together that function as a single column in effect. The diameter of the column can be any suitable diameter, such as less than or equal to 1 mm, 5 mm, 10 mm, 20 mm, 30 mm, 40 mm, 50 mm, 60 mm, 70 mm, 80 mm, 90 mm, 100 mm, 120 mm, 140 mm, 160 mm, 180 mm, 200 mm, 250 mm, 500 mm, 750 mm, 1 m, 2 m, 3 m, 4 m, 5 m, 6 m, 7 m, 8 m, 9 m, or about 10 m, or more.

The pH at which liquid chromatography is performed may be adjusted. For example, the pH at which liquid chromatography is performed may be in the range of about 2 to about 11.5. In some embodiments, the pH at which the liquid chromatography is performed may be in a range of about 2 to about 9.

Ammonium hydroxide may be injected into the liquid chromatography separation system and thus the impurities may be separated from ammonium hydroxide (S130). After injection of ammonium hydroxide into the liquid chromatography separation system, the passing (e.g. elution) of the mobile phase through the stationary phase may begin. During the elution process, mobile phase is added to the liquid chromatography separation system and allowed to flow through the stationary phase, after which the mobile phase can exit the system. As the mobile phase is passed through the system, the ammonium hydroxide and impurities in the mixture pass through the system at different rates depending on their relative attractions to the stationary phase versus the mobile phase. In an exemplary embodiment, the stationary phase of liquid chromatography separation system may have a weaker interaction with the impurities than with ammonium hydroxide. Accordingly, the impurities may be eluted from the liquid chromatography separation system earlier than ammonium hydroxide. The phrase of "the stationary phase interacts with a substance" may mean that "a functional group of the stationary phase interacts with the substance." When ammonium hydroxide has a concentration of more than about 5 wt %, a portion of ammonium hydroxide may not interact with the stationary phase. In this case, it may be difficult to carry out a quantitative analysis of the impurities. In some embodiments, ammonium hydroxide having a concentration of less than about 5 wt % may be injected into the liquid chromatography separation system and thus the impurities may be satisfactorily separated from ammonium hydroxide. In cases when the liquid chromatography is performed at a pH in the range of less than about 2 or more than about 11.5, the interaction between the impurities and the stationary phase may be substantially the same as or similar to that of interaction with the impurities and ammonium hydroxide. In some embodiments, the pH at which liquid chromatography is performed may be maintained in the range of about 2 to about 11.5, wherein the impurities may be easily separated from ammonium hydroxide. In some embodiments, the pH at which liquid chromatography is performed may be maintained in the range of about 2 to about 9. In some embodiments, deionized water or purified water may be used as a solvent such that an interaction between the stationary phase including functional groups represented by the chemical formula 1 and hydrogen peroxide may be distinct from an interaction between the stationary phase including functional groups represented by the chemical formula 1 and ammonium hydroxide.

A detector may be utilized to detect the impurities contained in an eluate flowing out of the liquid chromatography separation system (S140). For example, the detector may irradiate ultraviolet light on the eluate. The wavelength of the ultraviolet light is not particularly limited. For example, the ultraviolet light may be of a wavelength of 215 nm. The impurities within ammonium hydroxide may be quantitatively or qualitatively analyzed based on absorbance of the eluate is measured in relation to retention time. When ammonium hydroxide has a concentration of less than about 1 wt %, it may be difficult to carry out a qualitative analysis of the impurities. In some embodiments, ammonium hydroxide having a concentration of more than about 1 wt % may be injected into the liquid chromatography separation system.

Hereinafter, a method for detecting impurities in ammonium hydroxide will be explained with reference to Experimental Examples of the present inventive concept.

Detection of Impurities in Ammonium Hydroxide Using Liquid Chromatography

Comparative Example 1-1

Ammonium hydroxide including hydrogen peroxide as impurities is prepared to have a concentration of about 30 wt % and then the concentration thereof is adjusted to 3 wt %. A stationary phase is added to a solvent to prepare a liquid chromatography separation system. At this time, the stationary phase may include combined with a silica support, a functional group represented by the following chemical formula 2 that is combined with a surface of the silica support, and a functional group represented by the following chemical formula 3 that is combined with a surface of the silica support. Ammonium hydroxide including the impurities is injected into the liquid chromatography separation system while the pH at which the liquid chromatography is performed is maintained in the range of 2 to 9. Ultraviolet light is irradiated on the eluate and absorbance of the eluate is measured in relation to retention time.

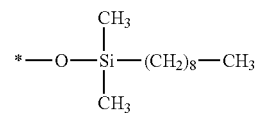

[Chemical Formula 2]

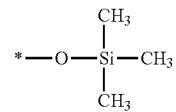

[Chemical Formula 3]

In the chemical formulae 2 and 3, a symbol of * means that a corresponding function group is combined with the silica support.

Comparative Example 1-2

Purified ammonium hydroxide without impurities is prepared and then its concentration is adjusted to 3 wt %. A liquid chromatography separation system is prepared to include a silica support and a functional group represented by the chemical formula 1 that is combined with a surface of the silica support. Ammonium hydroxide including hydrogen peroxide is injected into the liquid chromatography separation system while the pH at which the liquid chromatography is performed is maintained in the range of 2 to 11.5. Ultraviolet light is irradiated on the eluate and absorbance of the eluate is measured in relation to retention time.

Comparative Example 2-1

In the same manner as described in Comparative Example 1-2, ammonium hydroxide is injected into a liquid chromatography separation system and absorbance of the eluate is measured in relation to retention time. In this example, ammonium hydroxide is adjusted to have a concentration of 0.3 wt %.

Comparative Example 2-2

In the same manner as described in Comparative Example 1-2, ammonium hydroxide is injected into a liquid chromatography separation system and absorbance of the eluate is measured in relation to retention time. In this example, ammonium hydroxide is adjusted to have a concentration of 6 wt %.

Experimental Example 1

Ammonium hydroxide including impurities such as hydrogen peroxide is prepared in the same manner as described in Comparative Example 1-1. A stationary phase is added to water so as to prepare a liquid chromatography separation system. In this example, the stationary phase includes a silica support whose surface is combined with a function group represented by the chemical formula 1. Ammonium hydroxide including hydrogen peroxide is injected into the liquid chromatography separation system.

Ultraviolet light is irradiated on the eluate and absorbance of the eluate is measured in relation to retention time.

Experimental Example 2-1

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 20 ppm.

Experimental Example 2-2

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 50 ppm.

Experimental Example 2-3

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 100 ppm.

Experimental Example 2-4

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 5 ppm.

Experimental Example 2-5

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 7.5 ppm.

Experimental Example 2-6

In the same manner as described in Experimental Example 1, ammonium hydroxide is injected into a liquid chromatography separation system and absorbance of the eluate is measured in relation to retention time. In this example, ammonium hydroxide includes hydrogen peroxide at a concentration is 10 ppm.

Figure 2A:
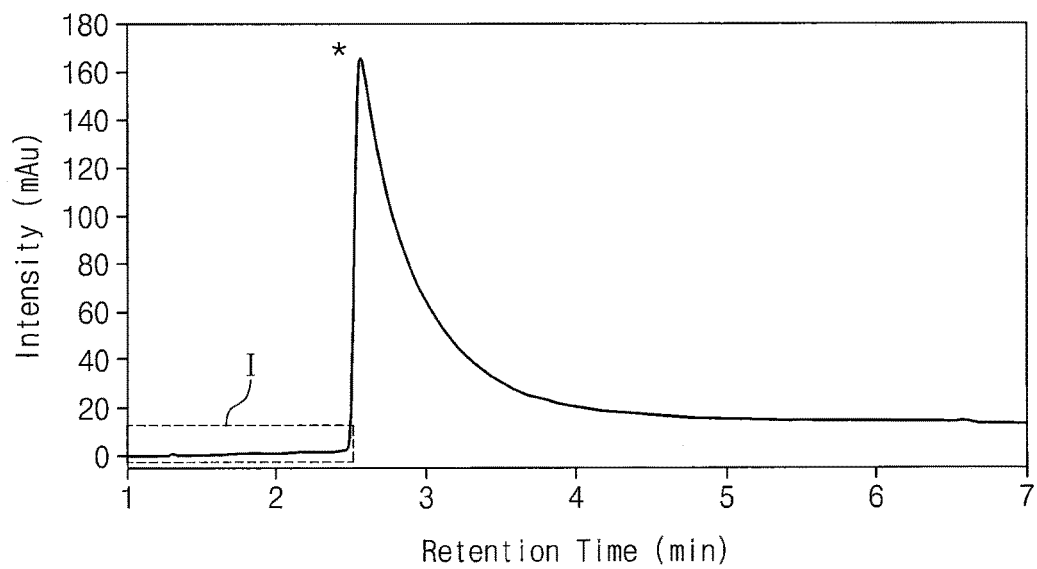
FIG. 2A is a graph showing absorbance versus retention time in Comparative Example 1-1.
Figure 2B:
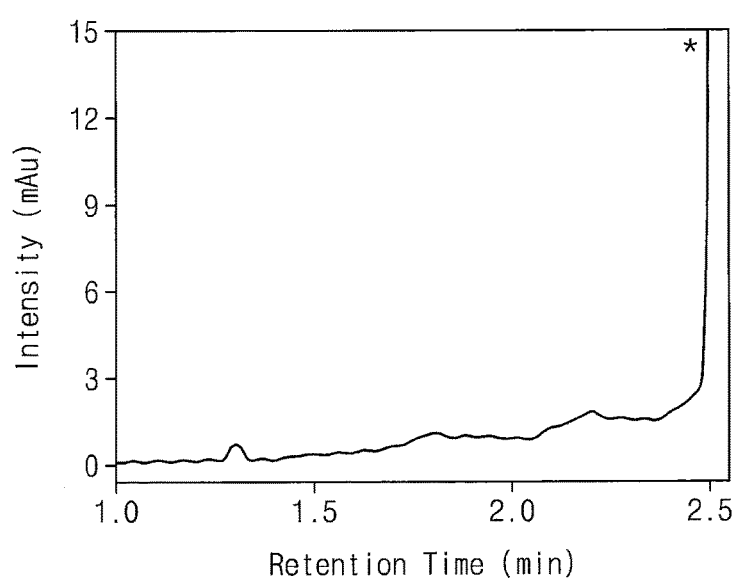
FIG. 2B shows an enlarged section I of FIG. 2A.

FIG. 2A is a graph showing absorbance versus retention time in Comparative Example 1-1. FIG. 2B shows an enlarged section I of FIG. 2A. In FIGS. 2A and 2B, a unit of mAu in relation to the vertical axis means a milli absorbance unit, which is also applicable to the following graphs.

Referring to FIGS. 2A and 2B, the peak (*) of ammonium hydroxide is observed and the peak of hydrogen peroxide is not observed in Comparative Example 1-1.

Figure 3A:
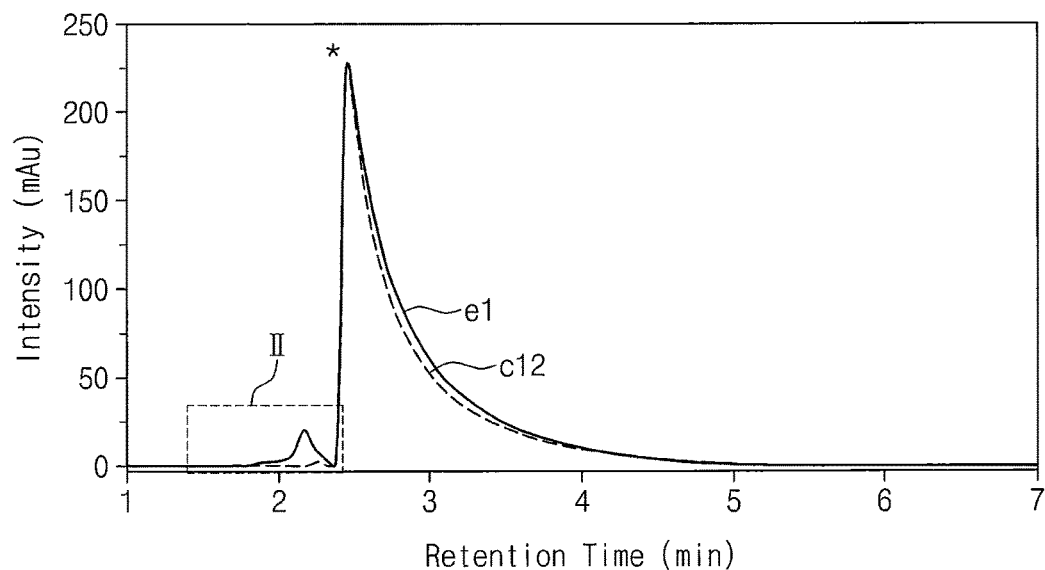
FIG. 3A is a graph showing absorbance versus retention time in Comparative Example 1-2 and Experimental Example 1.
Figure 3B:
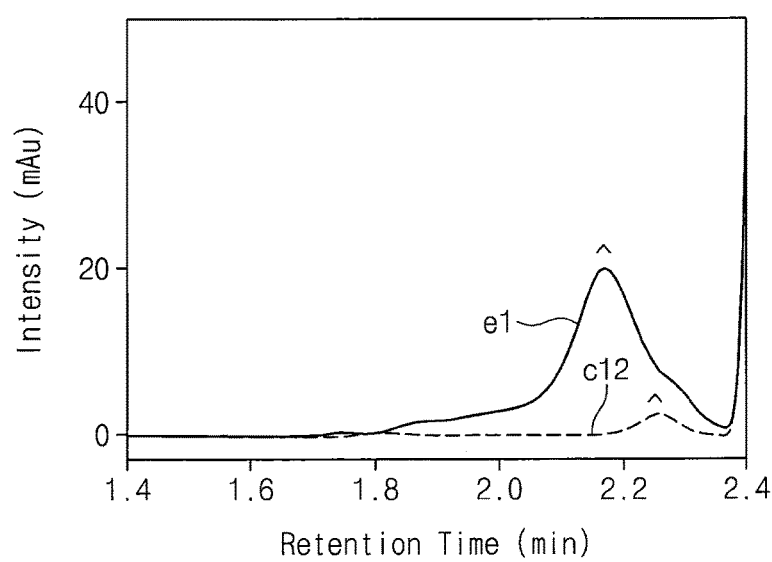
FIG. 3B shows an enlarged section II of FIG. 3A.

FIG. 3A is a graph showing absorbance versus retention time in Comparative Example 1-2 and Experimental Example 1. FIG. 3B shows an enlarged section II of FIG. 3A.

Referring to FIG. 3A, the peak (*) of ammonium hydroxide is observed in Comparative Example 1-2 (plotted as a dotted line c12) and Experimental Example 1 (plotted as a continuous curved line e1). Referring to FIG. 3B, the peak (^) of hydrogen peroxide is observed in Experimental Example 1 (e1) but not observed in Comparative Example 1-2 (c12). For these reason, it may be confirmed that the prepared ammonium hydroxide contains hydrogen peroxide as an impurity. Returning back to FIGS. 2A and 2B, the peak of hydrogen peroxide is not observed in Comparative Example 1-1 even though Comparative Example 1-1 uses ammonium hydroxide that is identical to that used in Experimental Example 1 (e1). It may be therefore found that impurities are contained in ammonium hydroxide used in Comparative Example 1-1 and the impurities are hard to be separated from ammonium hydroxide by the stationary phase used in Comparative Example 1-1. The stationary phase of Comparative Example 1-1 has the functional groups represented by the chemical formulae 2 and 3.

Referring back to FIGS. 3A and 3B, the stationary phase of Experimental Example 1 (e1) may include the silica support and the functional group represented by the chemical formula 1 that is combined with the silica support. The interaction between the stationary phase of Experimental Example 1 (e1) and hydrogen peroxide may be distinct from the interaction between the stationary phase represented by the chemical formula 1 and ammonium hydroxide. Accordingly, hydrogen peroxide may be easily separated from ammonium hydroxide.

Figure 4:
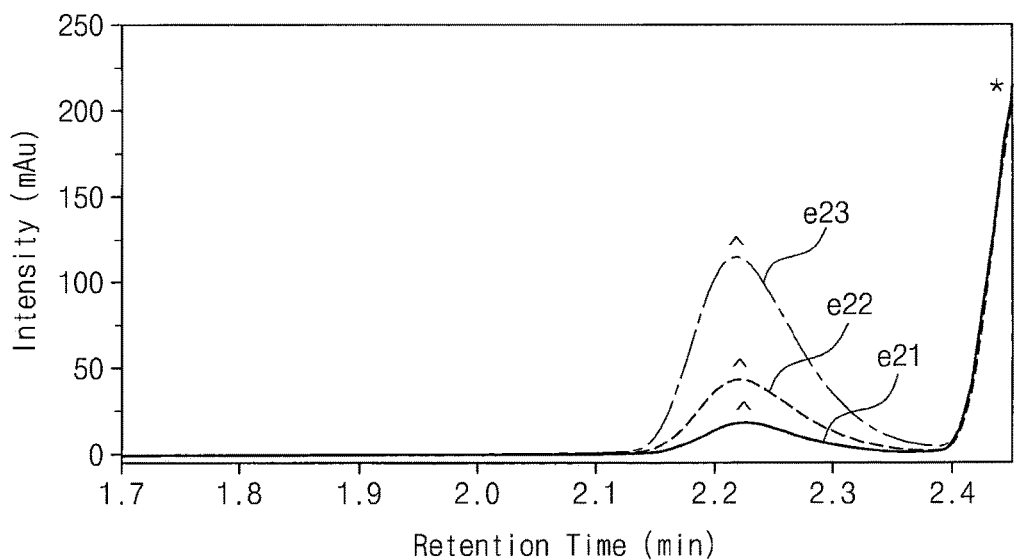
FIG. 4 is a graph showing absorbance versus retention time in Experimental Examples 2-1 to 2-3.

FIG. 4 is a graph showing absorbance versus retention time in Experimental Examples 2-1 to 2-3.

Referring to FIG. 4, the peak (*) of ammonium hydroxide and the peak (^) of hydrogen peroxide are respectively observed in each of Experimental Examples 2-1 (plotted as a dashed dotted line e2-1), 2-2 (plotted as a dotted line e22), and 2-3 (plotted as a continuous curved line e23). It may be found that retention time of hydrogen peroxide is shorter than retention time of ammonium hydroxide. It therefore may be verified that the stationary phase having the function group of the chemical formula 1 weakly interacts with hydrogen peroxide than with ammonium hydroxide.

Figure 5:
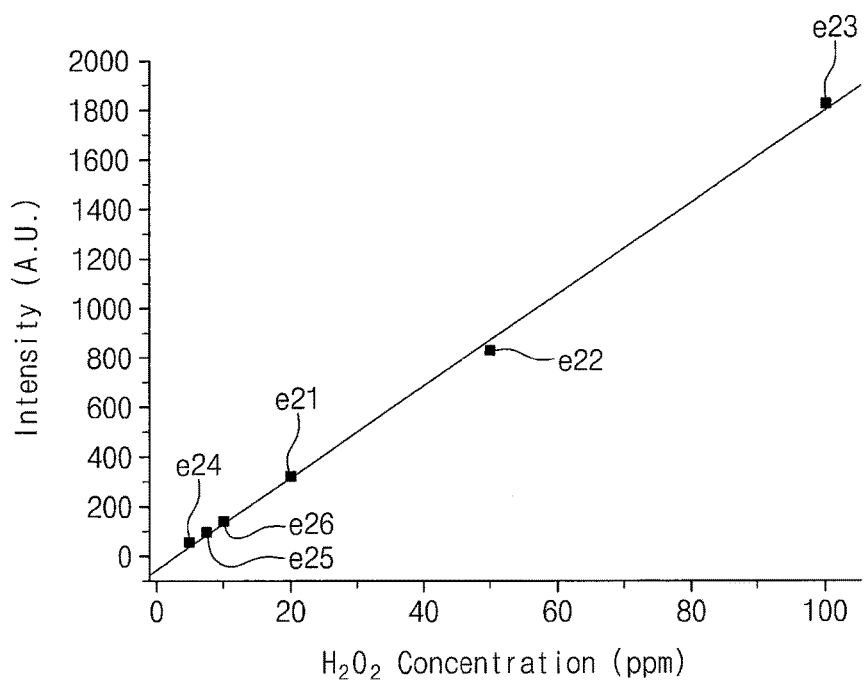
FIG. 5 is a graph showing the result of absorbance measurement according to concentration of hydrogen peroxide contained in ammonium hydroxide in Experimental Examples 2-1 to 2-6.

FIG. 5 is a graph showing the result of absorbance measurement according to concentration of hydrogen peroxide contained in ammonium hydroxide in Experimental Examples 2-1 to 2-6. In FIG. 5, the y axis represents a sum of absorbance intensity in an arbitrary unit, which corresponds to an area of peak of FIG. 4.

Referring to FIG. 5, it may be acknowledged that absorbance is proportional to concentration of hydrogen peroxide. Hydrogen peroxide may then be quantitatively analyzed by measuring absorbance of an eluate.

Figure 6A:
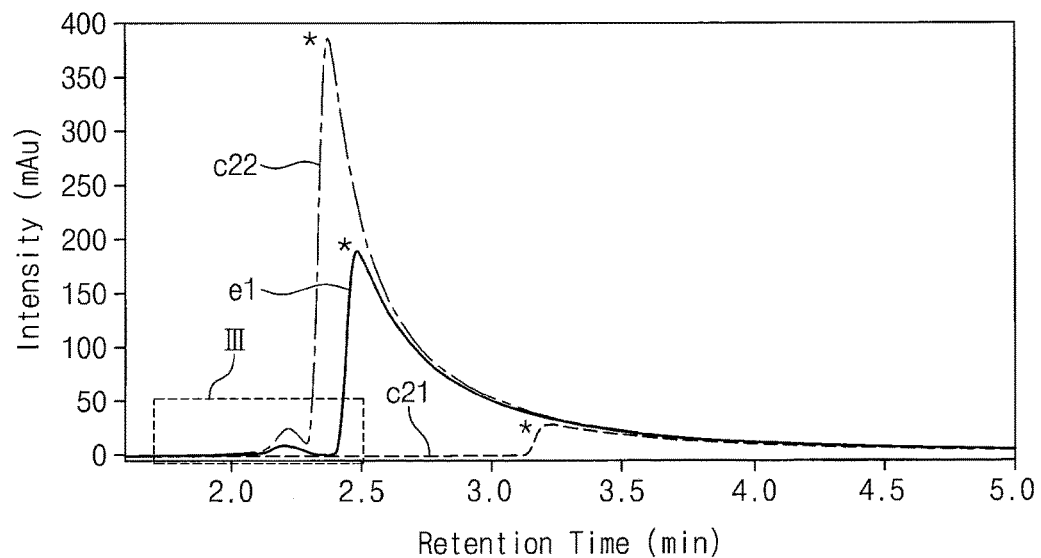
FIG. 6A is a graph showing absorbance versus retention time in Comparative Examples 2-1 and 2-2 and Experimental Example 1.
Figure 6B:
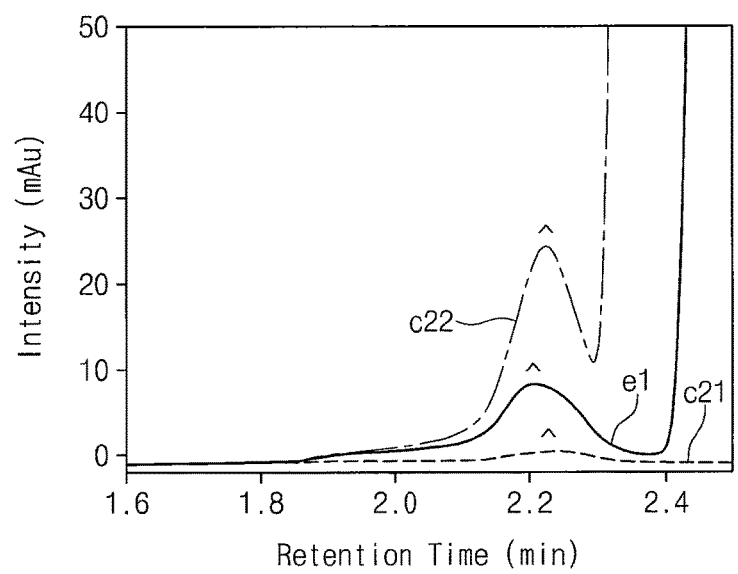
FIG. 6B shows an enlarged section III of FIG. 6A.

FIG. 6A is a graph showing absorbance versus retention time in Comparative Examples 2-1 and 2-2 and Experimental Example 1. FIG. 6B shows an enlarged section III of FIG. 6A.

Referring to FIGS. 6A and 6B, the peak (^) of impurities and the peak (*) of ammonium hydroxide are respectively observed in Comparative Example 2-1 (plotted as a dotted line c21), thereby reporting that it is possible to qualitatively analyze the impurities. However, it is hard to quantitatively analyze the impurities because of a low concentration thereof. The peak (^) of impurities and the peak (*) of ammonium hydroxide are respectively observed in Comparative Example 2-2 (plotted as a dashed dotted line c22), thereby stating that it is possible to qualitatively analyze the impurities. However, it is difficult to quantitatively analyze the impurities because that the peak (^) of the impurities partially overlap the peak (*) of ammonium hydroxide. The peak (^) of impurities and the peak (*) of ammonium hydroxide are respectively observed in Experimental Example 1 (plotted as a continuous curved line e1) such that it is acknowledged that a qualitative analysis of the impurities is possible. As the peak (^) of the impurities is separated from the peak (*) of ammonium hydroxide, it is possible to quantitatively analyze the impurities. In some embodiments, the impurities contained in ammonium hydroxide may be quantitatively analyzed using ammonium hydroxide whose concentration is in the range of 1 wt % to 5 wt %.

Figure 7:
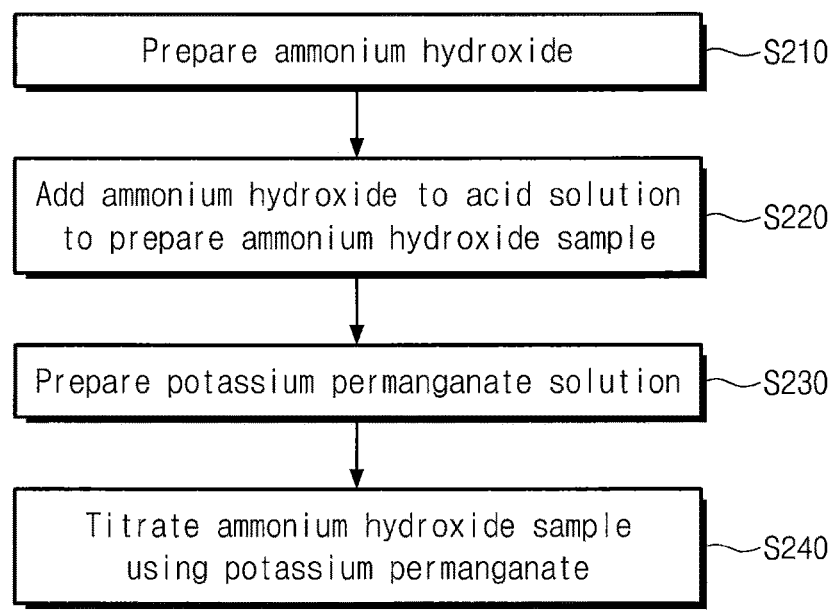
FIG. 7 is a flow chart showing a method for detecting impurities in ammonium hydroxide according to exemplary embodiments of the present inventive concept.

FIG. 7 is a flow chart showing a method for detecting impurities in ammonium hydroxide according to exemplary embodiments of the present inventive concept.

Referring to FIG. 7, ammonium hydroxide may be prepared (S210). Impurities may also be formed in the preparation of ammonium hydroxide. The impurities in ammonium hydroxide may include an oxidizer such as hydrogen peroxide ($H_2O_2$). Hydrogen peroxide is hereinafter exemplarily discussed as the impurities with reference to FIG. 7, but the present embodiment is not limited thereto. For example, the impurities may include various oxidizers that can react with potassium permanganate.

Ammonium hydroxide may be added to an acid solvent so as to prepare an ammonium hydroxide sample (S220). The ammonium hydroxide sample may have a pH in the range of less than about 3. For example, sulfuric acid may be used as the acid solvent. The ammonium hydroxide sample may include ammonia whose mass is more than a certain level and thus it may be possible to obtain an enhanced limit of detection for hydrogen peroxide contained in ammonium hydroxide. For example, ammonium hydroxide may be prepared to have a concentration of about 30 wt % and the ammonium hydroxide sample may include ammonium hydroxide whose content is more than about 1.5 g, specifically, in the range of about 1.5 g to about 1,000,000 g. The mass of ammonium hydroxide may be measured during its addition to the acid solvent. When the mass of ammonium hydroxide is measured prior to its addition to the acid solvent, ammonium hydroxide may be volatile. In this case, ammonium hydroxide may have mass for detection which is different from the measured mass thereof. In some embodiments, the mass of ammonium hydroxide may be measured during its addition to the acid solvent, which may prevent ammonium hydroxide from being volatile. Therefore, it may be obtained an enhanced accuracy of detection for impurities in ammonium hydroxide.

A potassium permanganate ($KMnO_4$) solution may be prepared (S230). Potassium permanganate may be adjusted to have a concentration per unit mass (1 g) of ammonia in the ammonium hydroxide sample. For example, potassium permanganate may have a concentration of about 0.1 mol/L.

Hydrogen peroxide in the ammonium hydroxide sample may be titrated by potassium permanganate. The potassium permanganate solution may be added several times to ammonium hydroxide to detect hydrogen peroxide in the ammonium hydroxide sample. Potassium permanganate and hydrogen peroxide may be reacted as described by the following reaction formula 1. The amount of hydrogen peroxide in the ammonium hydroxide sample may be qualitatively and quantitatively analyzed based on volume and concentration of the added potassium permanganate required to react with all of the hydrogen peroxide in the ammonium hydroxide sample according to reaction formula 1.

$$5H_2O_2 + 2KMnO_4 + 3H_2SO_4 \rightarrow K_2SO_4 + 2MnSO_4 + 5O_2 + 8H_2O \quad \text{[Reaction Formula 1]}$$

The prepared ammonium hydroxide may contain a very small amount of hydrogen peroxide. A detectable concentration of hydrogen peroxide may decrease with a concentration of potassium permanganate. The detectable concentration of hydrogen peroxide may decrease with an each addition amount of potassium permanganate. In some embodiments, potassium permanganate may be added by an amount of less than about 0.0015 mL, for example, about 0.0001 mL to about 0.0015 mL, for each time per unit gram (1 g) of ammonia in the ammonium hydroxide sample. Accordingly, it may be possible to enhance a limit of detection for hydrogen peroxide contained in ammonium hydroxide.

Hereinafter, a method for detecting impurities in the ammonium hydroxide will be explained with reference to Experimental Examples of the present inventive concept.

Detection of Impurities in Ammonium Hydroxide Using Titration

Comparative Example 3-1

Purified ammonium hydroxide is prepared to have a concentration of 30 wt %. The concentration of hydrogen peroxide in ammonium hydroxide is adjusted to 10 ppm by adding hydrogen peroxide to ammonium hydroxide. Ammonium hydroxide in the amount of 5.0 g is added to a sulfuric acid solution to prepare an ammonium hydroxide sample with a pH in the range of less than 3. A potassium permanganate solution at a concentration is 0.1 mol/L is added in the amount of 0.0020 mL for each time so as to titrate hydrogen peroxide in the ammonium hydroxide sample. A concentration of ammonium hydroxide is then calculated.

Comparative Example 3-2

In the same manner as described in Comparative Example 3-1, potassium permanganate is used to titrate hydrogen peroxide in the ammonium hydroxide sample. In this case, ammonium hydroxide in the amount of 1.0 g is added to a sulfuric acid solution and a potassium permanganate solution is added in the amount of 0.0005 mL for each time during the titration.

Comparative Example 3-3

In the same manner as described in Comparative Example 3-1, potassium permanganate is used to titrate hydrogen peroxide in the ammonium hydroxide sample. In this case, the potassium permanganate solution is added in the amount of 0.0030 mL for each time during the titration.

Comparative Example 3-4

In the same manner as described in Comparative Example 3-1, potassium permanganate is used to titrate hydrogen peroxide in the ammonium hydroxide sample. In this case, the potassium permanganate solution is added in the amount of 0.0040 mL for each time during the titration.

Comparative Example 3-5

In the same manner as described in Comparative Example 3-1, potassium permanganate is used to titrate hydrogen peroxide in the ammonium hydroxide sample. In this case, the ammonium hydroxide sample includes ammonium hydroxide of 0.5 g and the potassium permanganate solution is added in the amount of 0.0005 mL for each time during the titration.

Comparative Example 3-6

In the same manner as described in Comparative Example 3-1, potassium permanganate is used to titrate hydrogen peroxide in the ammonium hydroxide sample. In this case, the potassium permanganate solution is added in the amount of 0.0100 mL for each time during the titration.

Comparative Example 3-7

In the same manner as described in Comparative Example 3-1, potassium permanganate is used to titrate hydrogen peroxide in the ammonium hydroxide sample. In this case, the potassium permanganate solution is added in the amount of 0.0200 mL for each time during the titration.

Experimental Example 3-1

In the same manner as described in Comparative Example 3-1, potassium permanganate is used to titrate hydrogen peroxide in the ammonium hydroxide sample. In this case, ammonium hydroxide of 7.0 g is added to the sulfuric acid solution. The potassium permanganate solution is added in the amount of 0.0005 mL for each time during the titration.

Experimental Example 3-2

In the same manner as described in Experimental Example 3-1, potassium permanganate is used to titrate hydrogen peroxide in the ammonium hydroxide sample. In this case, ammonium hydroxide in the amount of 5.0 g is added to the sulfuric acid solution.

Experimental Example 3-3

In the same manner as described in Experimental Example 3-1, potassium permanganate is used to titrate hydrogen peroxide in the ammonium hydroxide sample. In this case, ammonium hydroxide in the amount of 3.0 g is added to the sulfuric acid solution.

Experimental Example 3-4

In the same manner as described in Experimental Example 3-1, potassium permanganate is used to titrate hydrogen peroxide in the ammonium hydroxide sample. In this case, ammonium hydroxide of 5.0 g is added to the sulfuric acid solution. The potassium permanganate solution is added in the amount of 0.0010 mL for each time during the titration.

Experimental Example 3-5

In the same manner as described in Experimental Example 3-1, potassium permanganate is used to titrate hydrogen peroxide in the ammonium hydroxide sample. In this case, ammonium hydroxide in the amount of 2.0 g is added to the sulfuric acid solution.

Experimental Example 3-6

In the same manner as described in Experimental Example 3-2, potassium permanganate is used to titrate hydrogen peroxide in the ammonium hydroxide sample. This case uses ammonium hydroxide containing hydrogen peroxide in the amount of 50 ppm.

Experimental Example 3-7

In the same manner as described in Experimental Example 3-2, potassium permanganate is used to titrate hydrogen peroxide in the ammonium hydroxide sample. This case uses ammonium hydroxide containing hydrogen peroxide in the amount of 100 ppm.

The following Table 1 shows concentrations of hydrogen peroxide detected in the ammonium hydroxide sample in Comparative Examples 3-1 to 3-7 and Experimental Examples 3-1 to 3-5. Potassium permanganate is represented by the number of moles per unit mass (1 g) of ammonia.

TABLE 1

| Example No. | The number of moles of $KMnO_4$ added for each time per 1 g of ammonia | Concentration of detected $H_2O_2$ (ppm) | Accuracy (%) | Difference (%) |
|---|---|---|---|---|
| Experimental 3-1 | 0.0021 | 10.6 | 106 | 6 |
| Experimental 3-2 | 0.0030 | 10.8 | 108 | 8 |
| Experimental 3-3 | 0.0051 | 10.8 | 108 | 8 |
| Experimental 3-4 | 0.0060 | 11.0 | 110 | 10 |
| Experimental 3-5 | 0.0075 | 11.2 | 112 | 12 |
| Comparative 3-1 | 0.0120 | 15.6 | 156 | 56 |
| Comparative 3-2 | 0.0150 | 13.3 | 133 | 33 |
| Comparative 3-3 | 0.0180 | 6.3 | 63 | 37 |
| Comparative 3-4 | 0.0240 | 14.5 | 145 | 45 |
| Comparative 3-5 | 0.0300 | 13.6 | 136 | 36 |
| Comparative 3-6 | 0.0600 | 13.2 | 132 | 32 |
| Comparative 3-7 | 0.1200 | undetected | — | — |

Referring to Table 1, it can be observed that Experimental Examples detect hydrogen peroxide in ammonium hydroxide at high precision. The accuracy of detecting hydrogen peroxide is better in Experimental Examples than in Comparative Examples. The accuracy of detection is a result indicating a percentage ratio of a concentration of detected hydrogen peroxide to a concentration (10 ppm) of hydrogen peroxide. In Experimental Examples, potassium permanganate is added more than 0.0001 mol for each time per 1 g of ammonia so as to enhance the accuracy of detecting hydrogen peroxide in the ammonium hydroxide sample. Mass of ammonium hydroxide, each injection volume of potassium permanganate, and concentration of potassium permanganate that are used in the titration may be adjusted. It therefore may be possible to control the number of moles of potassium permanganate added for each time per unit mass (1 g) of ammonia. For example, the number of moles of potassium permanganate added for each time may be in the range of about 0.0001 mol to about 0.01 mol, preferably about 0.0001 mol to about 0.0075 mol, per 1 g of ammonia in the ammonium hydroxide sample. Accordingly, it may be possible to obtain an enhanced limit of detection for impurities in the ammonium hydroxide sample.

The following Table 2 shows concentrations of hydrogen peroxide detected in the ammonium hydroxide sample in Experimental Examples 3-2, 3-6 and 3-7. Potassium permanganate is represented by the number of moles added for each time per unit mass (1 g) of ammonia.

TABLE 2

|  | Experimental Example No. | | |
| --- | --- | --- | --- |
|  | 3-2 | 3-6 | 3-7 |
| The number of moles of $KMnO_4$ added for each time per 1 g of ammonia | 0.0030 | 0.0030 | 0.0030 |
| Concentration of added $H_2O_2$ (ppm) | 10 | 50 | 100 |
| Concentration of detected $H_2O_2$ (ppm) | 11 | 52 | 102 |
| Accuracy (%) | 110 | 104 | 102 |
| Difference (%) | 10 | 4 | 2 |

Referring to Table 2, it can be observed that Experimental Examples highly precisely detect various concentrations of hydrogen peroxide at high precision. It may be possible to adjust the number of moles of potassium permanganate added for each time per unit mass (1 g) of ammonia so as to detect the various concentrations of hydrogen peroxide at high precision. Accordingly, it may be to obtain an enhanced limit of detection for hydrogen peroxide in the ammonium hydroxide sample.

According to present inventive concept, it can be possible to detect a very small amount of hydrogen peroxide in ammonium hydroxide. Also, it can be possible to obtain an enhanced limit of detection for impurities in ammonium hydroxide. It therefore may be provided a highly purified ammonium hydroxide.

Although the present invention has been described in connection with the embodiment of the present invention illustrated in the accompanying drawings, it is not limited thereto. It will be apparent to those skilled in the art that various substitution, modifications and changes may be thereto without departing from the scope and spirit of the invention.

What is claimed is:

1. A method for detecting impurities in ammonium hydroxide, the method comprising:
preparing ammonium hydroxide having a concentration in a range of 1 wt % to 5 wt %;
preparing a liquid chromatography separation system comprising a stationary phase and water;
injecting the ammonium hydroxide prepared having a concentration in a range of 1 wt % to 5 wt % into the liquid chromatography separation system; and
detecting whether impurities are present in the ammonium hydroxide injected into the liquid chromatography separation system,
wherein the stationary phase comprises:
silica; and
a functional group that is combined with a surface of the silica and is represented by the following chemical formula,

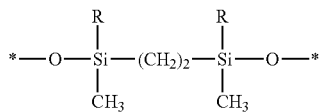

wherein, R is n-octadecyl, and a symbol of * means that the functional group is combined with the surface of the silica.

2. The method of claim 1, further comprising adjusting the liquid chromatography separation system to have a pH in a range of 2 to 11.5.

3. The method of claim 1, wherein the detecting whether impurities are present in the ammonium hydroxide comprises measuring absorbance of an eluate flowing out of the liquid chromatography separation system.

4. The method of claim 3, wherein the absorbance measured is ultraviolet light absorbance.

5. The method of claim 1, wherein the liquid chromatography is performed at a pH maintained in a range from about 2 to about 9.

6. The method of claim 1, wherein the stationary phase of the liquid chromatography system has a weaker interaction with the impurities than with ammonium hydroxide.

7. The method of claim 1, wherein the impurities comprise hydrogen peroxide.

8. A method for detecting impurities in ammonium hydroxide, the method comprising:
injecting ammonium hydroxide having a concentration in a range of 1 wt % to 5 wt % into a liquid chromatography separation system; and
detecting whether impurities are present in the ammonium hydroxide injected into the liquid chromatography separation system,
wherein the liquid chromatography separation system comprises a stationary phase and water; and wherein the stationary phase comprises silica and a functional group combined with a surface of the silica having the following chemical formula:

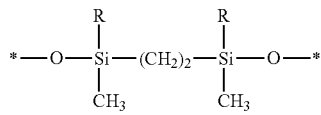

wherein, R is n-octadecyl, and a symbol of * means that the functional group is combined with the surface of the silica.

9. The method of claim 8, further comprising adjusting the liquid chromatography separation system to have a pH in a range of about 2 to about 11.5.

10. The method of claim 8, wherein the detecting whether impurities are present in the ammonium hydroxide comprises measuring absorbance of an eluate flowing out of the liquid chromatography separation system.

11. The method of claim 10, wherein the absorbance measured is ultraviolet light absorbance.

12. The method of claim 8, wherein the impurities comprise hydrogen peroxide.

13. The method of claim 1, wherein the method can detect impurities present at a concentration of about 5 ppm to about 100 ppm in the ammonium hydroxide.

14. The method of claim 8, wherein the method can detect impurities present at a concentration of about 5 ppm to about 100 ppm in the ammonium hydroxide.

* * * * *